(12) United States Patent
Miescher et al.

(10) Patent No.: US 7,887,797 B2
(45) Date of Patent: Feb. 15, 2011

(54) IMMUNOGLOBULIN FRACTIONS

(75) Inventors: Sylvia Miescher, Bern (CH); Reinhard Franz Bolli, Worb (CH)

(73) Assignee: CSL Behring AG, Bern (CH)

( * ) Notice: Subject to any disclaimer, the term of this patent is extended or adjusted under 35 U.S.C. 154(b) by 419 days.

(21) Appl. No.: 11/666,690

(22) PCT Filed: Oct. 27, 2005

(86) PCT No.: PCT/EP2005/011494

§ 371 (c)(1),
(2), (4) Date: May 1, 2007

(87) PCT Pub. No.: WO2006/048174

PCT Pub. Date: May 11, 2006

(65) Prior Publication Data

US 2009/0028846 A1  Jan. 29, 2009

(30) Foreign Application Priority Data

Nov. 2, 2004  (EP)  .................................. 04025936

(51) Int. Cl.
*A61K 39/00* (2006.01)
(52) U.S. Cl. .................................................. 424/130.1
(58) Field of Classification Search .................. None
See application file for complete search history.

(56) References Cited

U.S. PATENT DOCUMENTS 6,090,380 A * 7/2000 Weisbart ................... 424/130.1
6,231,856 B1  5/2001 Williams

FOREIGN PATENT DOCUMENTS

EP  1 394 183 A1  3/2004

OTHER PUBLICATIONS

Van Mirre et al (J Immunology, Jul. 2004, 173:332-339, IDS).*
Tankersley et al (Molecular Immunology, 1988, 25:41-48, IDS).*
Vassilev, T.L., et al., "Variable Region-Connected, Dimeric Fraction of Intravenous Immunoglobulin Enriched in Natural Autoantibodies," *Journal of Autoimmunity*, London, GB, vol. 8, No. 3, 1995, pp. 405-413.
Tankersley, D.L., et al., "Immunoglobulin G Dimer an Idiotype-Antiidiotype Complex," *Molecular Immunology*, vol. 25, No. 1, 1988, pp. 41-48.

Roux, K.H., et al., "A View of the Human Idiotypic Repertoire Electron Microscopic and Immunologic Analyses of Spontaneous Idiotype-Anti-Idiotype Dimers in Pooled Human IgG," *Journal of Immunology*, vol. 144, No. 4, 1990, pp. 1387-1395.
Miescher, S.M., et al., "Comparative Analysis of Antigen Specificities in the Monomeric and Dimeric Fractions of Intravenous Immunoglobulin," *Annals of the New York Academy of Sciences*, Jun. 2005, vol. 1051, pp. 582-590.
Teeling, J.L., et al., "Therapeutic Efficacy of Intravenous Immunoglobulin Preparations Depends on the Immunoglobulin G Dimers: Studies in Experimental Immune Thrombocytopenia," *Blood*, vol. 98, No. 4, Aug. 15, 2001, pp. 1095-1099.
Tankersley, D.L., "Dimer Formation in Immunoglobulin Preparations and Speculations on the Mechanism of Action of Intravenous Immune Globulin in Autoimmune Diseases," *Immunological Reviews*, vol. 139, Jun. 1994, pp. 159-172.
Bayry et al., "Inhibition of Maturation and Function of Dendritic Cells by Intravenous Immunoglobulin," Blood, vol. 101, No. 2, pp. 758-765, 2003.
De Grandmont et al., "Intravenous Immunoglobulins Induce the in vitro Differentiation of Human B Lymphocytes and the Secretion of IgG," Blood, vol. 101, No. 8, pp. 3065-3073, 2003.
Kazatchkine et al., "Immunomodulation of Autoimmune and Inflammatory Diseases with Intravenous Immune Globulin," New England Journal of Medicine, vol. 345, No. 10, pp. 747-755, 2001.
Lazarus et al., "Mechanism of Action of IVIG and Anti-D in ITP," Transfusion and Apheresis Science, vol. 28, No. 3, pp. 249-255, 2003.
Samuelsson et al., "Anti-Inflammatory Activity of IVIG Mediated Through the Inhibitory Fc Receptor," Science, American Association for the Advancement of Science, vol. 291, No. 5503, pp. 484-486, 2001.
Shoham-Kessary et al., "Immune complex-Like Moieties in Immunoglobulin for Intravenous Use (IVIg) Bind Complement and Enhance Phagocytosis of Human Erythocytes," Clinical and Experimental Immunology, vol. 113, No. 1, pp. 77-84, 1998.
Van Mirre et al., "Monomeric IgG in Intravenous Ig Preparations Is a Functional Antagonist of FcyRII and FcyRIIIb," Journal of Immunology, vol. 173, No. 1, pp. 332-339, 2004.
European Search Report mailed on Feb. 14, 2008.
Mahoney R.J. and Breggia A.E., "Inhibition of HLA Antibody Cytotoxicity by Intravenous Immunoglobulin G F(ab')$_2$ Dimers, Monomers, and Monovalent F(ab)," Human Immunology, 60:492-99 (1999).

(Continued)

*Primary Examiner*—Laura B Goddard
(74) *Attorney, Agent, or Firm*—Finnegan, Henderson, Farabow, Garrett & Dunner, L.L.P.

(57) ABSTRACT

The present invention relates to novel pharmaceutical compositions comprising fractions of human immunoglobulin preparations, novel applications of these compositions and a method for manufacturing the compositions.

16 Claims, 16 Drawing Sheets

OTHER PUBLICATIONS

Sylvia M. Miescher, et al., "Comparative Analysis of Antigen Specificities in the Monomeric and Dimeric Fractions of Intravenous Immunoglobulin," *Annals of the New York Academy of Sciences*, vol. 1051, pp. 582-590, 2005.

Coutinho A. et al., "Natural Autoantibodies," Curr Opin Immunol, 7(6), pp. 812-818, 1995.

Cohen, I.R., "The Cognitive Paradigm and the Immunological Homunculus," Immunol Today 13(12), pp. 490-494, 1992.

Haeney, M., "Intravenous Immune Globulin in Primary Immunodeficiency," Clin Exp Immunol, 97, pp. 11-15, 1994.

Sewell, W.A. et al., "Immunomodulatory Action of Intravenous Immunoglobulin," Immunology, 107(4), pp. 387-393, 2002.

Rossi, F., et al., "Anti-Idiotypes against Autoantibodies in Normal Immunoglobulins: Evidence for Network Regulation of Human Autoimmune Responses," Immunol Rev, 110, pp. 135-149, 1989.

Simon, H.U., et al., "IVIG—Mechanisms of Action," Allergy, 58(7), pp. 543-552, 2003.

Ginaldi, L., et al., "The Immune System in the Elderly: Activation-Induced and Damage-Induced Apoptosis," Immunol Res, 30(1), pp. 81-94, 2004.

Lacroix-Desmazes, S., et al., "Analysis of the Natural Human IgG Antibody Repertoire: Life-long Stability of Reactivities Towards Self Antigens Contrasts with Age-dependent Diversification of Reactivities Against Bacterial Antigens," Eur J Immunol, 25(9), pp. 2598-2604, 1995.

European Search Report for Application No. 04025936.8-2406, mailed Apr. 12, 2005.

Invitation to Pay Additional Fees for PCT/EP2005/011494 mailed May 30, 2006, from the International Searching Authority of the European Patent Office.

International Search Report and Written Opinion for PCT/EP2005/011494, mailed Nov. 29, 2006, from the International Searching Authority of the European Patent Office.

International Search Report and Written Opinion for PCT/EP2005/011494, mailed Jul. 18, 2007, from the International Searching Authority of the European Patent Office.

Partial European Search Report for Application No. 09002383.9-2406, mailed Apr. 17, 2009.

European Search Report for Application No. 09002383.9-2406 / 2062915, mailed Jun. 22, 2009.

* cited by examiner

F1 = 40% dimers, 40% monomers
F2 = 86.3% dimers, 13.7% monomers
F3 = 11.3% dimers, 88.7% monomers
F4 = 100% monomers HPLC profiles of IVIG Fractions

Figure 8

**Reactivity to M5 protein of *S. pyogenes* in IVIG fractions**

Figure 13

FACS profiles of COS-7 (HEP-G2, HEp-2, CHO) cells

IMMUNOGLOBULIN FRACTIONS

CROSS REFERENCE TO RELATED APPLICATIONS

This application is a National Phase application of International Application No. PCT/EP2005/011494 filed under the Patent Cooperation Treaty on Oct. 27, 2005, which claims the benefit of European Patent Application No. 04025936.8, filed Nov. 2, 2004, the disclosures of which are incorporated in their entireties.

The present invention relates to novel pharmaceutical compositions comprising fractions of human immunoglobulin preparations, novel applications of these compositions and a method for manufacturing the compositions.

Intravenous immunoglobulin (IVIG) preparations are derived from pooled plasma of thousands of healthy donors (current pool sizes range from 1000-60,000) and contain both immune and natural antibodies (NAbs) reflecting the cumulative antigen experience of the donor population. IVIG thus contains a large spectrum of so-called "immune antibodies" specificities directed against pathogens and foreign antigens as well as NAbs reacting with self/autoantigens. NAbs are so defined as they are generated in the absence of deliberate immunization and independently of exposure to foreign antigens (1). Indeed a long list of antibodies to self antigens has been detected and even purified by affinity chromatography from IVIG preparations. These NAbs are often polyreactive, can bind to pathogens and by tagging and clearing senescent or altered molecules and cells from the circulation are important in maintaining immunohomeostasis (2). Further, it has been proposed that these NAbs recognise a conserved subset of immunodominant antigens referred to as the immunological homunculus that is essential for maintaining tolerance to self (3). However, a more precise characterisation of these antibodies, their properties and their potential presence in a sub-fraction of IVIG has not been defined partly due to the paucity of knowledge on the relevant target antigens and antibodies.

Current therapeutic applications of IVIG cover 2 major categories: i) antibody replacement in primary and secondary antibody deficiencies (4) ii) immunomodulation in patients with systemic inflammatory and autoimmune diseases (2, 5). While IVIG has shown clinical efficacy in the antibody deficiencies and in some autoimmune and inflammatory diseases [(for example Immune Thrombocytopenic Purpura (ITP), Guillain Barré Syndrome (GBS), Kawasaki disease, Chronic Inflammatory Demyelineating Polyneuropathy (CIDP)] there are many examples of unconfirmed/equivocal clinical benefits in other autoimmune and systemic inflammatory conditions often due to lack of statistically significant controlled trials.

The mode of action of IVIG is complex involving modulation of the expression and function of Fc receptors, interference with complement activation and the cytokine network, modulation of activation, differentiation and effector functions in many different cell types. The idiotype network has been proposed as an essential network involved in immune homeostasis with imbalances eventually leading to overt autoimmune disease. Many of the current therapeutic indications for IVIG are based on counterbalancing, neutralising or blocking pathological autoimmune antibodies and thus restoring a healthy idiotype network (6, 7). Recent reports have also shown direct effects on monocytes, dendritic cells, endothelial and both T and B lymphocytes. This complexity reflects the essential functions of circulating antibodies in maintaining homeostasis in healthy individuals (2, 8).

There are many reports in the literature demonstrating the decrease in immune reactivity with age, so called immunosenescence (9). However it appears that there is a life long stability of natural IgG antibodies reacting with self antigens compared to an age dependent diversification of IgG antibody repertoires to foreign antigens with increasing age (10).

IVIG consists of intact IgG molecules with an IgG isotype distribution corresponding to that of normal human serum and trace amounts of IgA. Depending on the formulation, IVIG preparations contain variable amounts of monomeric and dimeric IgG. Monomers represent the monomeric IgG (ca. molecular weight 150,000) while dimers represent 2 IgG molecules which from previous data can be orientated as classical idiotype anti-idiotype pairs (11).

EP-A-1394183 discloses a method to purify autoantibodies from IVIG preparations using affinity chromatography on a ligand, e.g. a mixture of proteins present in human serum other than immunoglobulin bound to a solid support.

U.S. Pat. No. 6,231,856 discloses human antibody compositions comprising substantially purified and concentrated anti-idiotypic antibodies or antigen-binding fragments thereof for the treatment of antibody-based autoimmune diseases. The antibody compositions are obtained by affinity chromatography.

According to the present invention, it was found that a size fractionation of a human immunoglobulin preparation gives a fraction of dimeric antibodies and a fraction of monomeric antibodies, which have different characteristics. The dimeric fraction shows an increased reactivity to antigens, e.g. self-antigens and/or exoantigens. Further, the dimeric fraction contains antibodies with higher affinity to target antigens and thus may have a higher biological activity, e.g. neutralizing activity in the case of anti-bacterial, anti-toxin or anti-viral activities. In contrast thereto, the monomeric fraction may contain lower affinity antibodies, e.g. natural antibodies, i.e. the basic repertoire from which high affinity antibodies develop.

In a first aspect, the present invention relates to a pharmaceutical composition comprising a fraction of human antibodies or antigen-binding fragments thereof from a heterogeneous human donor population wherein the fraction originates from the dimeric human antibodies.

In a further aspect, the present invention relates to a pharmaceutical composition comprising a fraction of human antibodies or antigen-binding fragments thereof from a heterogeneous human donor population wherein the fraction originates from the monomeric human antibodies.

The fractions may be obtained from any preparation comprising polyclonal human antibodies preparation from a plurality of donors. Preferably, the fractions are obtained from an IVIG preparation.

In this context, an IVIG preparation is a human immunoglobulin preparation which may be derived from pooled plasma of a plurality, e.g. 1,000-100,000 of blood donors. Antigen-binding fragments of the antibodies may be obtained by known methods, e.g. by proteolytic digestion. Preferred antibody fragments are Fab fragments or F(ab')$_2$ fragments.

The monomeric or dimeric fractions may be obtained by size fractionation of human antibody preparations. The size fractionation may comprise size exclusion separation, gel filtration, ultrafiltration, diafiltration and/or other gel or membrane separation methods. The monomeric fraction may be obtained by recovering antibody monomers with an apparent molecular weight of about 150 kDa and the dimeric fraction may be obtained by recovering antibody dimers with an apparent molecular weight of about 300 kDa.

Preferably, the size fractionation comprises size exclusion chromatography, e.g. on a Superose 6 or a Sephacryl S-300 column.

The purity of the monomeric and dimeric fractions obtained by size fractionation may be measured by analytical HPLC, e.g. size exclusion chromatography on a TSK G 3000 SWXL column.

The purity of dimeric antibody fraction is usually at least 75%, preferably at least 80% and more preferably at least 85% as determined by analytical HPLC wherein the analysis is preferably carried out immediately after size fractionation.

The purity of monomeric antibody fraction is usually at least 85%, preferably at least 90% and more preferably at least 95% as determined by analytical HPLC, wherein the analysis is preferably carried out immediately after size fractionation.

The dimeric antibody fraction is preferably characterized by an increased reactivity to exoantigens such as tetanus toxoid and/or respiratory syncytial virus (RSV) and/or the Toxin A of *Pseudomonas aeruginosa* and/or autoantigens such as red blood cell ghosts and/or Hep-2 epithelial cells. More particularly, the dimeric fraction may have an at least two times increased specific activity against tetanus toxoid and/or respiratory syncytial virus compared to an unfractionated IVIG preparation as determined in the examples section. Further, the dimeric fraction may have an at least two times increased reactivity towards an M virulence protein of *S. pyogenes* and/or Hep-2 epithelial cells in particular to the intracellular antigens compared to an unfractionated IVIG preparation as determined in the examples section.

The pharmaceutical composition of the dimeric antibody fraction may comprise antibodies in a dimeric form or in a dissociated or (re)monomerised form. Preferably the antibodies are in a dissociated or (re)monomerised form, wherein the content of dimers is 10% or less, more preferably 5% or less. Monomerisation may be carried out by adjusting an acidic pH, e.g. an pH in the range of about 3 to about 5, preferably about 3.5 to about 4.5, more preferably a pH of about 4.0. The pH may be adjusted by any pharmaceutically acceptable acidic buffering agent, e.g. acetic acid. The monomerised preparation of dimeric antibodies is preferably dynamically stable and substantially does not reconvert to dimers under the above-indicated conditions of storage and use as determined in the examples section.

The dimeric fraction contains antibodies with a higher specific activity than the monomeric fraction. Thus, this fraction is preferably used for the manufacture of a medicament against infections by a pathogen, e.g. viral, bacterial, fungal, protozoal and/or parasital infections. Especially preferred is the use of the dimeric fraction for the treatment of acute infections.

A further preferred application for dimeric fraction is a manufacture of a medicament against autoimmune disorders, e.g. and/or for the maintenance of autoimmune homeostasis. The dimeric fraction contains idiotypic and anti-idiotypic antibodies, which are important for maintaining an internal equilibrium. The dimers show a physiological auto reactivity, which is kept under control by the corresponding anti-idiotypic antibodies to avoid clonal expansion of auto reactive clones leading to autoimmune disease. For example the monomerised dimeric fraction compared to either unfractionated IVIG or the monomeric fraction shows an increased activity against loop 2 of the muscarinic 3 receptor (M3R), one of the target antigens of Sjögren's Syndrome as determined in the Examples section. This activity is only revealed when the idiotypic and anti-idiotypic antibodies in the dimeric fraction are monomerised.

Due to the high specific activity, the dimeric fraction may be administered in low doses resulting in higher compatibility and less side effects. Preferably, in this embodiment of the invention, the preparation is administered in a dose which is sufficient to obtain a therapeutic effect without causing undesired side effects.

The monomeric fraction on the other hand comprises both immune and natural antibodies but without the anti-idiotypic antibodies and would be of particular benefit to maintain and boost an ailing immune system. A preferred application is the administration to children, senior persons or immunocompromised persons, e.g. persons suffering from disorders diminishing the immune system or undergoing a therapy diminishing the immune system. Especially preferred is the administration for anti-aging and/or rejuvenation therapy. It was also surprisingly found, that the monomeric fraction has an increased reactivity to polysaccharides of microorganisms, especially to polysaccharides of different serotypes of *Pseudomonas aeruginosa*.

It is therefore another aspect of the invention to use the monomeric fraction for the manufacture of a medicament against infectious microorganisms preferentially for the treatment of infections by *Pseudomonas aeruginosa*.

The dimer content of the monomer preparation is preferably limited to a maximum amount of 7%, preferably 2.5%, and more preferably 1% in order to avoid adverse reactions for the treatment groups.

Still a further aspect of the present invention is a method for manufacturing pharmaceutical compositions comprising fractions of human antibodies or antigen-binding fragments thereof from a heterogeneous human donor population comprising:

(a) subjecting a human antibody preparation from a heterogeneous donor population to a size fractionation, (b) recovering a fraction of dimeric antibodies and optionally monomerising the dimeric antibodies and (c) recovering a fraction of monomeric antibodies.

The monomeric fraction is characterized by having a molecular weight of about 150 kDa in the size fractionation procedure. The dimeric fraction is characterized by having a molecular weight of about 300 kD in the size fractionation procedure.

Further, the invention shall be explained in more detail by the following examples.

FIGURES AND TABLES

FIG. 1

Optimization of Chromatography and Fractionation of IVIG Preparations

Various columns were tested as above using different flow rates (FR), different buffer systems and varying loading capacity for a 12% Sandoglobulin (SAGL) preparation. Fractions were collected and analysed by analytical HPLC for content of monomers, dimers and aggregates.

FIG. 2

Preparative Fractionation of IVIG Preparations

A Sephacryl S-300 column (dimensions 26/60) was equilibrated in PBS/0.92% azide, followed by application of 500 ml of a 12% Sandoglobulin (SAGL) preparation. The column was run at a flow rate of 1.2 ml/min and fractions 1-4 collected as indicated above and analysed by analytical HPLC for content of monomers, dimers and aggregates. This column allowed a scale up at the laboratory scale for preparation of monomer and dimer fractions.

FIG. 3

Profiles of IVIG and Separated Monomeric and Dimeric Fractions on Analytical HPLC An analytical HPLC was used to analyse the % dimers, monomers and aggregates in the different fractions: IVIG freshly dissolved from a SAGL 12% preparation; monomeric and dimeric fractions isolated on a Sephacryl S-300 column. The dotted line shows the dimers and monomers found in unseparated SAGL.

FIG. 4

Kinetics of Separated Dimer Fractions

The separated dimer fraction was kept at room temperature and analysed at intervals over a maximal time span of 48 h, (range shown 0-24 h) to observe the stability of the dimer fraction with respect to dissociation into monomers. The solid line represents the % dimers in the dimeric fraction, the dotted line represents the % monomers in the dimeric fraction.

FIG. 5

Flow Chart for the Size Exclusion Separation of Monomers and Dimers in IVIG

FIG. 6

Optimal pH Conditions for Preparation of Monomerised Dimer Fractions

Dimeric and monomeric fractions were collected and dialyzed for 24 h at 4° C. at pHs ranging from 4 to 7 using either citrate phosphate buffers from pH 2.6-7 or 10 mM acetic acid buffer, pH4. Dialysis was performed using Spectra/Por 4 Dialysis Membranes with a 12,000-14,000 molecular weight cut-off (MWCO) (Spectrum Laboratories, Rancho Dominguez, Calif.) or a Mini Dialysis Kit with a MWCO of 8,000 (Amersham Biosciences, Uppsala, Sweden). Analytical HPLC was performed immediately after dialysis. Panels A, B, C: HPLC profiles of the dialyzed dimeric fractions are shown: dimers pH 4 (A), dimers pH 5 (B) and dimers pH 7 (F): Panels D, E, F: HPLC profiles of the dialyzed monomeric fractions are shown: monomers pH 4 (D), monomers pH 5 (E) and monomers pH 7 (F).

FIG. 7

2D PAGE Analysis of Separated Monomer and Dimer Fractions

Two-dimensional polyacrylamide electrophoresis was performed as previously described in 2D-Electrophoresis, Principles and Methods (Amersham Biosciences). In brief, 4 µg of total IVIG, monomeric and dimeric Immunoglobulin (Ig) fractions were diluted in 125 µl of rehydration buffer containing 8M urea, 2% CHAPS, 0.002% bromphenol blue, DTT (0.65 mM) and IPG Buffer 0.5%, each. 7 cm IPG strips pH 3-10 (Amersham Biosciences), were rehydrated overnight and focused on an IPGphor unit (Amersham Biosciences), according to the strip specifications (step 1: constant 300V/60 min, step 2: gradient to 1000V/30 mins, step 3: gradient to 5000 V/90 min, step 4: constant 5000V/15 min). The focused strips were equilibrated in two steps of 15 minutes in equilibration buffer containing 50 mM Tris-HCl, pH 8.8, 6M urea, 30% (v/v) glycerol, 2% (v/v) SDS, 0.002% (v/v) bromphenol blue and either 10 mg/ml DTT ($1^{st}$ equilibration) or 25 mg/ml iodoacetamide ($2^{nd}$ equilibration). For the molecular weight separation, the strips were rinsed in sodium dodecyl sulfate (SDS) running buffer containing 2.5 mM Tris (hydroxymethyl)-aminoethan (Merck), 25 mM Glycin (Merck), 0.01% SDS (w/v) (Flucka) and placed on a 12% polyacrylamide gel. Subsequently, the strips were overlayed with a 4% polyacrylamide stacking gel and the second dimension was run on a MiniProtean electrophoresis chamber (BioRad) at a constant 100V for approximately 90 minutes. Silver staining was performed using the PlusOne silver staining kit (Amersham Biosciences).

FIG. 8

Reactivity to M5 Protein of *S. pyogenes* in IVIG Fractions

ELISA: antigens (recombinant human M proteins: M1, M3, M5, M6, M19,) coated at 10 µg/ml. Blocking PBS/casein 2 hr 37° C. First antibody (IVIG T0/IVIG pH4.0/dimers/monomers) at 10, 100 and 100 µg/ml: 4 hr at 37° C. Second antibody: AP004 (Binding Site) Sheep anti-human IgG Peroxidase, 1/1000 (2 h, 37° C.). Results are shown for M5, which is representative of all other M proteins.

FIG. 9

Differential Activity of Dimeric Fraction on Exoantigens. Increased Activity of Dimeric Fraction Correlates with Increase in Affinity of Binding Affinity measurements against Tetanus toxoid and M1 protein. The affinities of different IVIG preparations were assessed by online monitoring using the IAsys cuvette system. The cuvettes were immobilized with 5 µg of either recombinant M1 protein from *Streptococcus pyogenes* (*S. pyogenes*) or Tetanus toxoid. To measure the association the IVIG preparations were diluted to different concentrations in PBS/0.05% Tween 20 and added in 50 µl samples to the cuvettes. The cuvettes were washed with 3×50 µl PBS/0.05% Tween 20 for monitoring the dissociation of antibodies. For regeneration the cuvettes were washed sequentially 3 times with 40 µl 20 mM HCl for 2 minutes and with 45 µl PBS/0.05% Tween 20. The $K_D$ was calculated by plotting the $k_{on}$ values obtained for each concentration of IVIG, monomers or dimers using the FAST plot and the Grafit programs.

ELISA: IVIG, monomer and dimer fractions were analysed using commercial kits for Tetanus toxoid, respiratory syncytial virus (RSV) and *H. influenzae* B and the results expressed according to the units/g Immunoglobulin (Ig) calculated from a standard curve. Activity to the M1 protein was titrated out as described in FIG. 7.

FIG. 10

Dimers Show an Increased Neutralising Activity against RSV in a Functional Neutralisation Assay using HEp-2 Cells The neutralizing action of different IVIG preparations ($IVIG_{total}$ at pH7 and at pH4, monomers at pH4 and dimers at pH4) were pre-diluted to 1.5 mg/ml and serially diluted out in duplicates on 96 well plates (Becton Dickinson, Meylan Cedex, FR). After adding 50 µl of a RSV Long fraction (½ $10^5 TCID_{50}$/ml) to each well, the antibody-virus mixtures were incubated for 1 hour at room temperature (on a shaker; sealed with parafilm). All dilutions were performed in fully supplemented DMEM. The amount of virus required for the assay was defined previously as the quantity of RSV particles ($500 TCID_{50}$/ml) resulting in 100% cell death after 3 days. HEp-2 cells (ATCC CCL23) were cultured in 96 well-plates (Becton Dickinson, Meylan Cedex, FR) and grown to 20 000 cells/well. Subsequently, the culture medium was removed and the previously incubated antibody-virus mixture was transferred to the HEp-2 cells and incubated for approximately 72 hours at 37° C. in a humidified atmosphere.

The cell culture medium was removed from the HEp-2 cells and the cells were washed twice with PBS, pH 7.4. The cells were fixed with methanol-acetone (1:1 ratio, pre-cooled to 4° C.) for 10 minutes at 4° C. The cells were washed again with PBS, pH7.4. They were covered with 50 µl of a monoclonal mouse anti-RSV FITC labeled antibody (Chemicon Europe LTD., Southampton, UK) per well. The labeled antibody was incubated for 1 hour at 37° C., in the dark. The excess antibody was washed away twice with PBS, pH7.4 and once with distilled $H_2O$. After the staining, one drop of fluorescence mounting fluid (Chemicon Europe LTD., Southampton, UK) was added and the infection was visualised at a ×20 magnification under a fluorescence microscope (Nikon, Eclipse TE300, Egg/ZH, CH). Images were captured with a digital camera (Nikon, Digital Camera DXM1200, Egg/ZH, CH) using an image analysis software (ACT-1, Nikon, Egg/ZH, CH).

FIG. 11

Dimers Show Increased Activity on loop 2 Peptide of Muscarinic 3 Receptor, a Target Antigen of Sjögren's Syndrome IVIG preparations (IVIG$_{total}$ at pH7 and at pH4, monomers at pH4 and dimers at pH4 were compared in ELISAs (as described previously for FIG. 8) using a synthetic peptide representing loop 2 of M3R.

FIG. 12

Dimers show a Preferential Increased Activity on Intracellular as Compared to Extracellular Self Antigens Monomers and dimers at pH 4 used at a concentration of 100 µg/ml were compared in ELISAs (as described previously for FIG. 8) using antigens representing intracellular and extracellular proteins coated at 10 µg/ml.

FIG. 13

Monomers Show a Preferential Reactivity to the Various Lipopolysaccharide Serotypes (IATS) of *Pseudomonas aeruginosa* whereas the Reverse was Found for Toxin A

*Pseudomonas aeruginosa* LPS serotypes (International Antigen Typing System) and Toxin A were assayed by standard ELISA. Each plate contained serial dilutions of a reference antibody preparation (plasma pooled of 9 individuals immunized with 8 valent *Pseudomonas aeruginosa* O-polysaccharides toxin A conjugate vaccine), control plasma and test samples (monomers and dimers). The reference antibody was used as the basis for quantitating the amount of anti-LPS or anti-toxin A IgG antibody concentration in the control plasma and the test samples

FIG. 14

Dimers show Increased Activity on Cytoskeletal Proteins Immunofluorescence on HEp-2 Cells For immunohistology 50 µl of IVIG, monomeric and dimeric Ig fractions were incubated on a diagnostic ANA (HEp-2 actin) slide (INOVA Diagnostics, Inc., San Diego, US) for 30 minutes at 200 µg/ml, followed by a 5 minute washing step in PBS. Subsequently, the FITC labeled anti-human IgG conjugate (INOVA Diagnostics, Inc., San Diego, US) was incubated for 20 minutes, followed by another 5 minute wash in PBS. Images were acquired at a 400× magnification on a fluorescence microscope (Nikon E600, Eclipse), employing the ACT-1 software (Nikon).

FIG. 15

Dimers Show an Increased Autoreactivity on HepG2 Cells

HepG2 (hepatoma) cells were grown to confluence in DMEM culture medium supplemented with 10% FCS. The cells were trypsinized and washed twice in PBS, before lysis. The cellular proteins were subjected to trichloracetic acid precipitation ready for subsequent 2D-PAGE using the same procedure described previously for FIG. 7. The resulting two-dimensional gels (see silver stain, 1.a, upper panel) were transferred to nitrocellulose, blocked with PBS containing 0.15% casein and incubated over night at 4° C. with monomeric (1.b, middle panel) or dimeric (1.c, lower panel) IgG fractions at 10 µg/ml. Development was performed using an alkaline phosphatase conjugated goat-anti-human IgG antibody at 1:1000 in PBS-casein (0.15%) and an alkaline phosphatase development kit (BioRad Inc.).

FIG. 16

Dimers Show Increased Activity on Intracellular Proteins of Epithelial Cells from Different Animal Species FACS analysis of epithelial cells from monkey (COS-7), human (HEP-G2, HEp-2) and hamster (CHO). Rat basophilic leukemia cells wild type (RBL wt) were used as control non-epithelial cells (FACS profiles not shown).

For flow cytometry all adherent cell lines were detached with PBS-EDTA 0.03% (w/v), fixed with 1% (v/v) paraformaldehyde in PBS-casein 0.15% (w/v) (Sigma, Buchs, Switzerland) and permeabilized with 0.3% saponin (Sigma, Buchs, Switzerland) (w/v) in PBS-casein 0.15% (w/v). The indirect staining was performed in a duplicate multi-step procedure: (1) incubation of non-permeabilized or permeabilized cells for 20 minutes with 50 µg of IVIg, monomeric or dimeric Ig fractions in either PBS-casein 0.15% (w/v) or PBS-casein 0.15%/saponin 0.3% (both w/v), respectively. (2) Incubation with isotype specific FITC-labeled sheep anti-human IgG-FC (PFO04, The Binding Site, Birmingham) for 20 minutes. Both incubations were followed with two 5 minute washing steps in PBS. Flow cytometric data acquisition was done on a FACSCalibur machine using Cell Quest Pro software (both Becton-Dickinson), and for subsequent data analysis WinMDI software (©Joseph Trotter) was employed.

TABLE 1

Differential reactivity of separated monomeric and dimeric fractions on selected antigens

| Exoantigens | Immunoglobulin fractions | | Self-antigens | Immunoglobulin fractions | |
|---|---|---|---|---|---|
| | Monomers | Dimers | | Monomers | Dimers |
| Tetanus toxoid[ab] | + | ++ | Myosin[b] | + | ++ |
| Diphtheria toxoid[a] | + | + | Phosphorylase B[b] | + | ++ |
| Campylobacter jejuni[a] | + | + | Fibronectin[b] | − | − |
| E. coli[a] | + | +/− | α2-macroglobulin[b] | + | + |
| Bacteriophage[a] | + | + | C-reactive protein[a] | + | + |
| KLH[ab] | + | + | IgE, IgA, IgM[a] | +/− | +/− |
| Bovine serum albumin[a] | +/− | +/− | Human serum albumin[a] | − | − |
| Streptavidin[a] | − | − | Erythropoietin[a] | − | − |
| | | | FcεRI-αchain[a] | +/− | +/− |
| | | | C1q[a] | + | + |

Results summary from immunodot blots[a] and ELISA[b].

Immunodots: air-dried dots with 10, 100 and 500 ng Antigen. Blocking: Top block, 1,5 h, room temperature (RT). First antibody (dimers/monomers) at 10, 100 and 500 µg/ml: over night at 4° C. Second antibody: AP004 (Binding Site) Sheep anti-human IgG Peroxidase (2 h, RT).

Reactivities:

+ strong reaction of 100 µg/ml immunoglobulin preparations on 10 ng antigen dots +/− weak reactivity of 500 µg/ml immunoglobulin preparations on 500 ng antigen dots − no reactivity of 500 µg/ml immunoglobulin preparations on 500 ng antigen dots ELISA: antigens coated at 10, 1 µg/ml. Blocking PBS/casein 2 hr 37° C. First antibody (dimers/monomers) at 10, 100 and 1000 µg/ml: 4 hr at 37° C. Second antibody: AP004 (Binding Site) Sheep anti-human IgG Peroxidase, 1/1000 (2 h, 37° C.).

Reactivities: comparison of reactivity at 10 µg/ml antigen with 100 µg/ml immunoglobulin fractions. ++ dimer signal titrates out at least logfold more than monomers, +clear signal over background, +/– weak signal but still above background, – no signal.

EXAMPLES

We have investigated the differential reactivities of the monomeric and dimeric fractions found in IVIG preparations. We have used a lyophilized preparation which was solubilised according to the instructions for clinical in vivo use. This IVIG, also called SAGL, (short form for Sandoglobulin) was then aliquoted and stored at –20° C. for further experiments. This IVIG was used as a reference in all further assays and to establish the conditions for separation of the monomeric and dimeric fractions. Our results have indicated a differential reactivity pattern of these fractions against both self/auto- and exo-antigens, which has been confirmed using a variety of techniques.

1) Isolation of the Monomeric and Dimeric Fractions of IVIG:

To optimize the fractionation we tested several different column types (Sephacryl, Superose, ReproSil) and different conditions (buffers, flow rates, size of columns). The Sephacryl S-300, a semi-preparative HPLC system, combined good peak separation, high purity of the fractions, short run times and high protein concentrations in the fractions, see FIGS. 1 and 2. The separated fractions were immediately analysed by HPLC, as shown in FIG. 3. In agreement with previous reports we observed that dimers demonstrate a dynamic instability (i.e. tend to revert to the monomeric form) influenced by buffer, pH, temperature, protein concentration and storage time. FIG. 4 shows the kinetics of decay of the separated dimer fraction when stored at room temperature. The dimeric IgG reduced within hours to a more stable dimeric population, range 20-30% of the original dimers. In general, the formation of dimers is slow whereas their decay is faster. In contrast the monomeric fraction is stable over many weeks and does not re-form dimers.

2) Preparation of a Dissociated Dimer Preparation:

In order to produce a dimeric fraction that is dynamically stable and that would imitate the in vivo dissociation of dimers once injected a dissociated dimeric fraction was used which is effectively converted into its monomeric components. The optimal pH condition was tested by dialyzing both dimers and monomers (for control purposes) against buffers at pHs ranging from 4 to 7. Dialysis was followed immediately by HPLC analysis of the dialyzed fractions. As shown in FIG. 6 the optimal pH for dissociation of the dimers was pH4 (remaining dimer content reduced to less than 10%) whereas dialysis at pH 5 and 7 resulted in remaining dimer contents of 39.41% and 55.19% respectively. The monomer fraction is remarkably stable under all pH conditions tested. This means the dimeric fraction is separated by size exclusion followed by a treatment (in our e.g. we used a dialysis into acetic acid at pH 4.0) to convert the dimeric IgG into monomers. This required a minimum of 24 h dialysis into 10 mM acetic acid pH 4.0. Thereafter, this dissociated dimer preparation contained less than 5% dimers, remained dynamically stable and does not re-convert to dimers under defined conditions of storage and use. Further, neutralization of the dissociated dimers to pH 7.4 in PBS buffer had no effect on the % dimers after up to 24 h storage even at room temperature. Thus for the duration of the assay conditions used to assess reactivity, the dissociated dimers would remain dissociated. To allow equal comparison of monomers and dimers the monomers were also subjected to the same treatment and compared in the same buffer system. An example of an optimized flow chart for the separation and preparation of the various fractions used is shown in FIG. 5.

3) Characterisation of the Monomeric and Dissociated Dimer Preparations

Both fractions demonstrated the expected overall patterns for heavy and light chains on 2D gel electrophoresis. The dimeric fraction showed a tendency for a wider isoelectric distribution extending more into the acidic region, FIG. 7. Comparative isotype analysis showed equal distribution of IgG1, 2, 4 and slightly increased IgG3 in the dimeric fractions.

4) Differential Reactivities of Monomeric and Dissociated Dimer Preparations

Reactivities to both exo- and self/auto-antigens in a range of different assays have been performed. In summary, the dimeric fraction shows an increased reactivity to certain antigens both self-antigens and exoantigens. In some cases we have also measured the affinity of the reaction, which was clearly increased in the dimers. We have not found an antigen specificity where the reactivity is only present in either the monomers or the dimers. There are antigens where no detectable antibody reactivity was detected in either the monomers or the dimers.

FIG. 8 shows results from an ELISA using, human recombinant M5 protein (virulence factors) of *Streptococcus pyogenes*. The dimers show a clearly enhanced reaction compared to either the monomers or the IVIG preparations defined as T0 (IVIG prepared and frozen at Time zero) or IVIG defined as pH4.0 (IVIG dialysed into the same buffer as the dimers).

Figure 1:
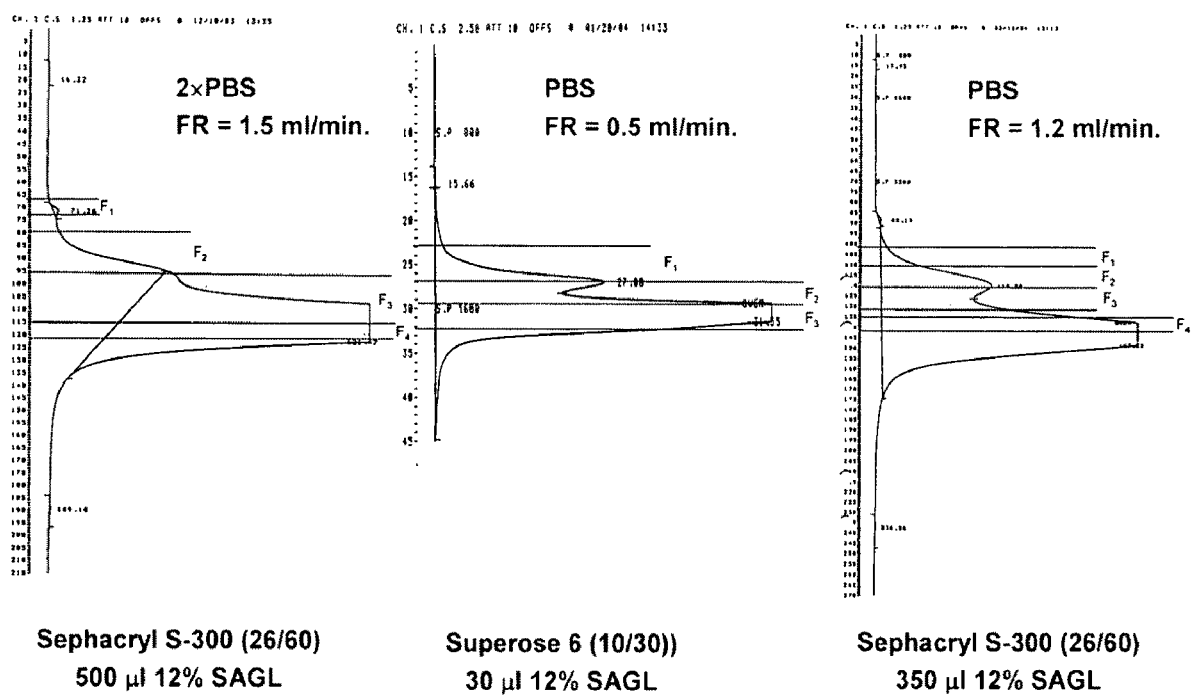
Figure 2:
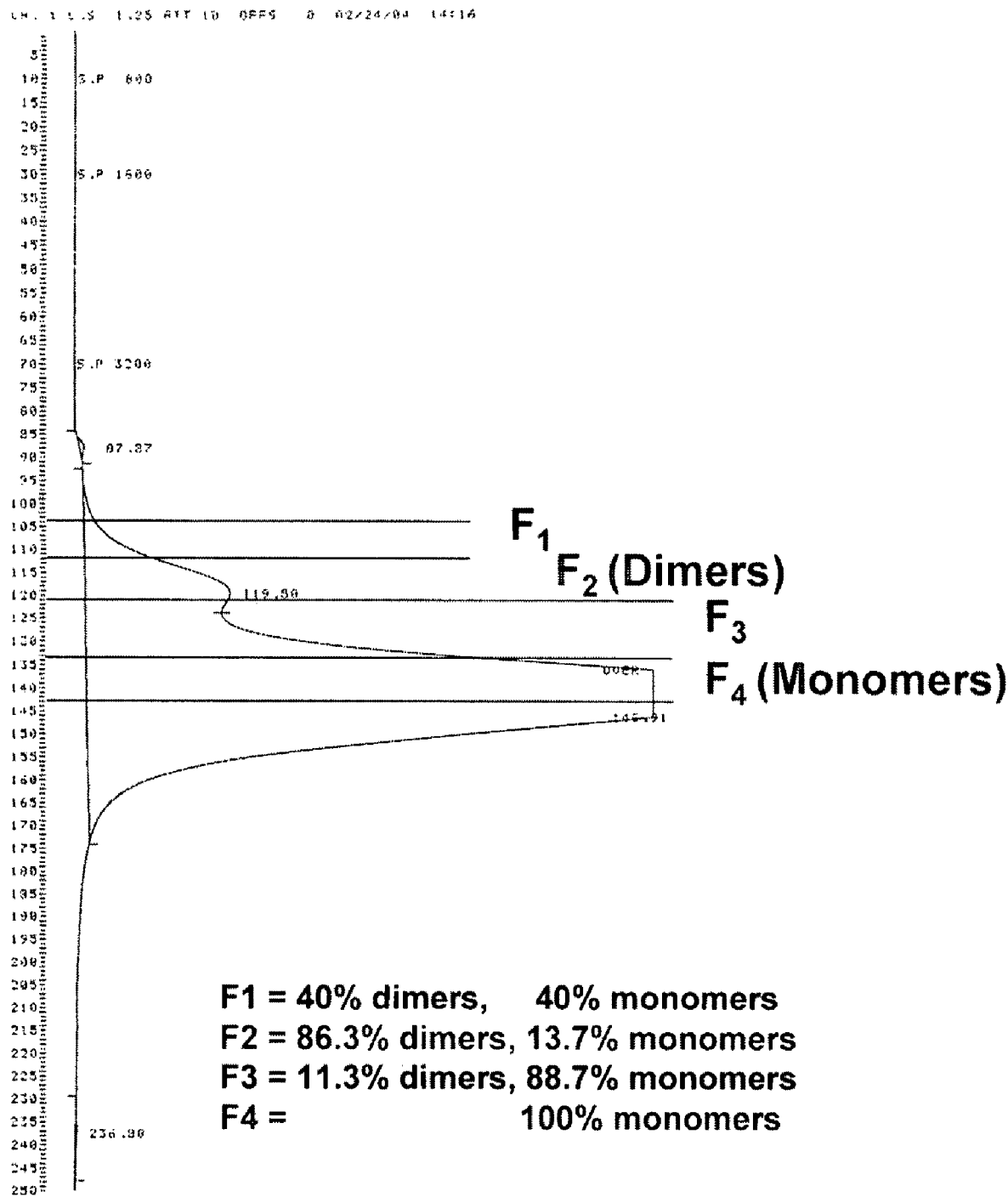
Figure 3:
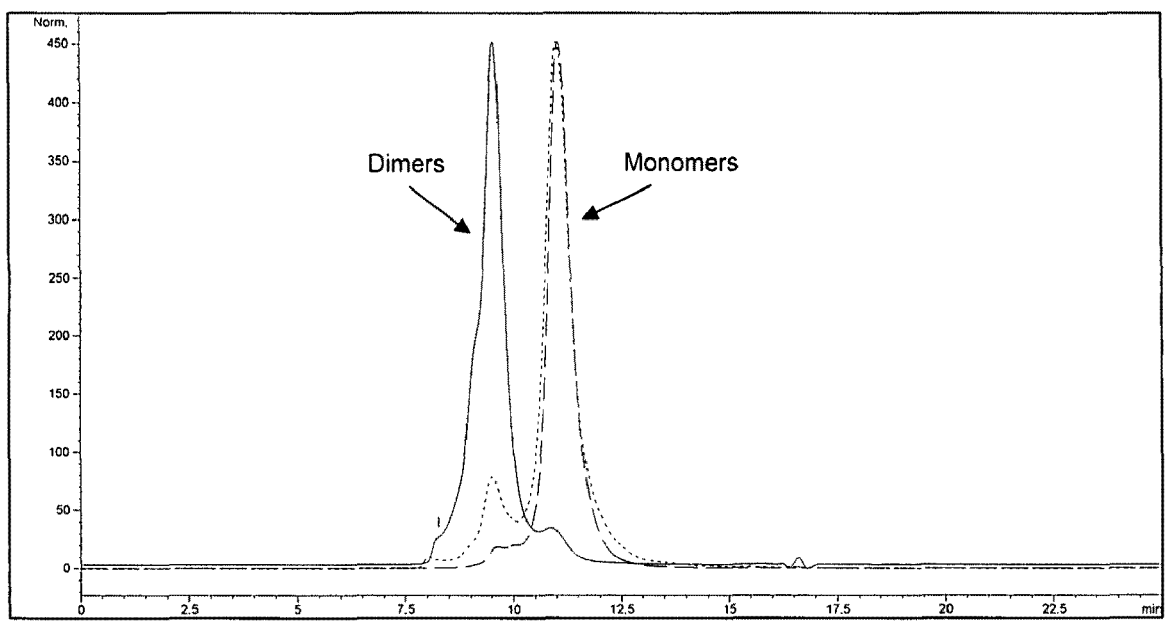
Figure 4:
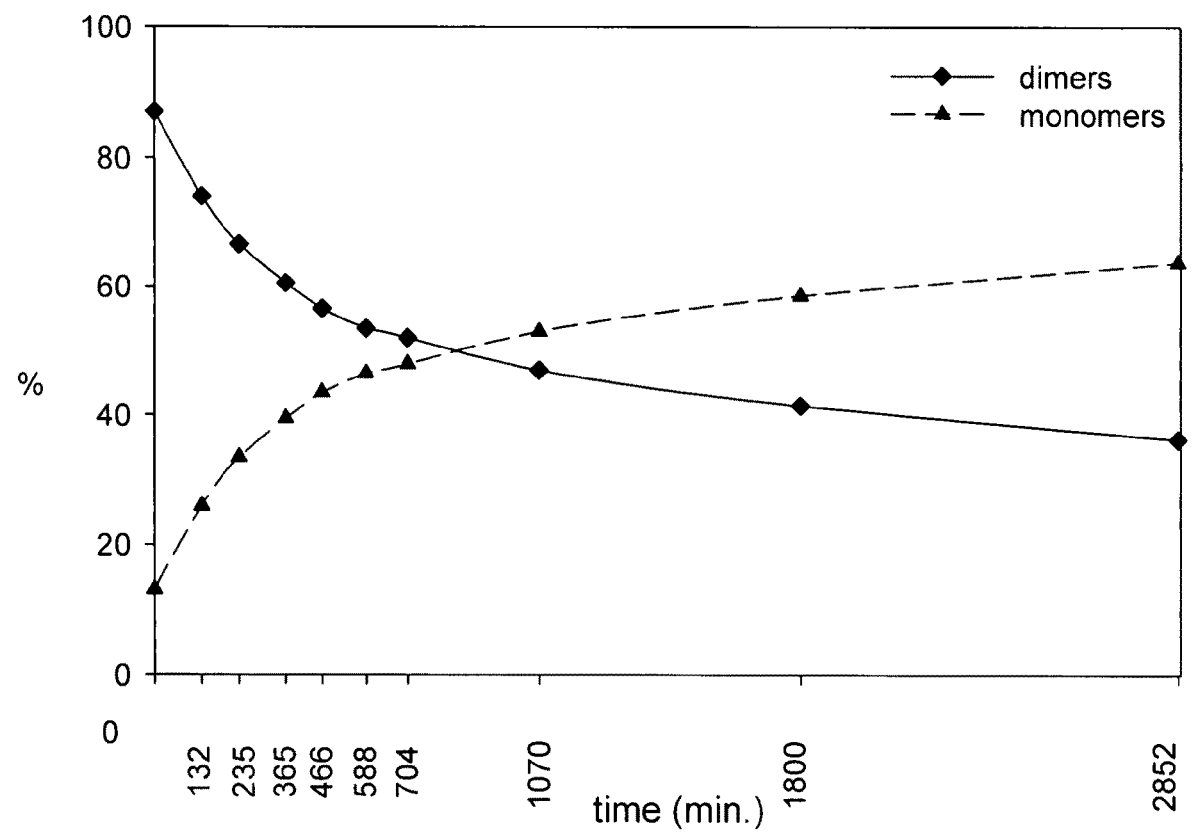
Figure 5:
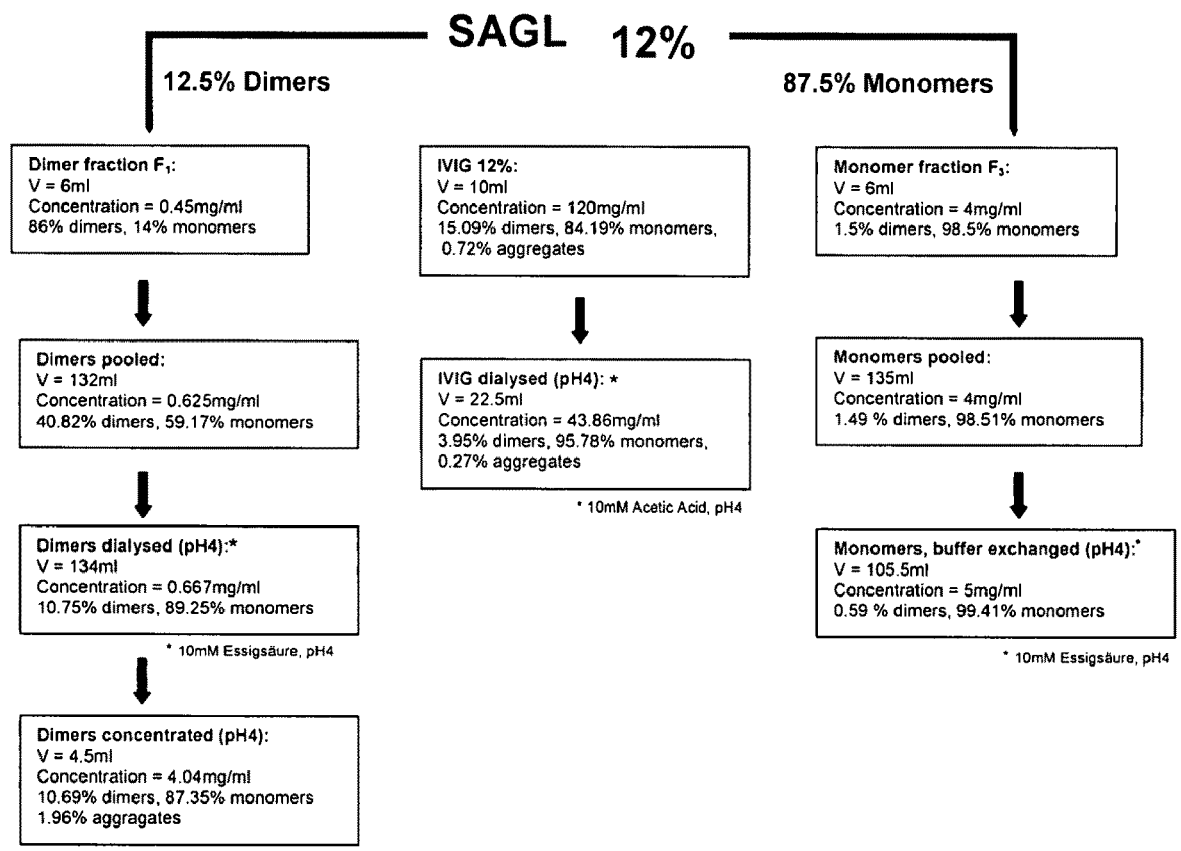
Figure 6:
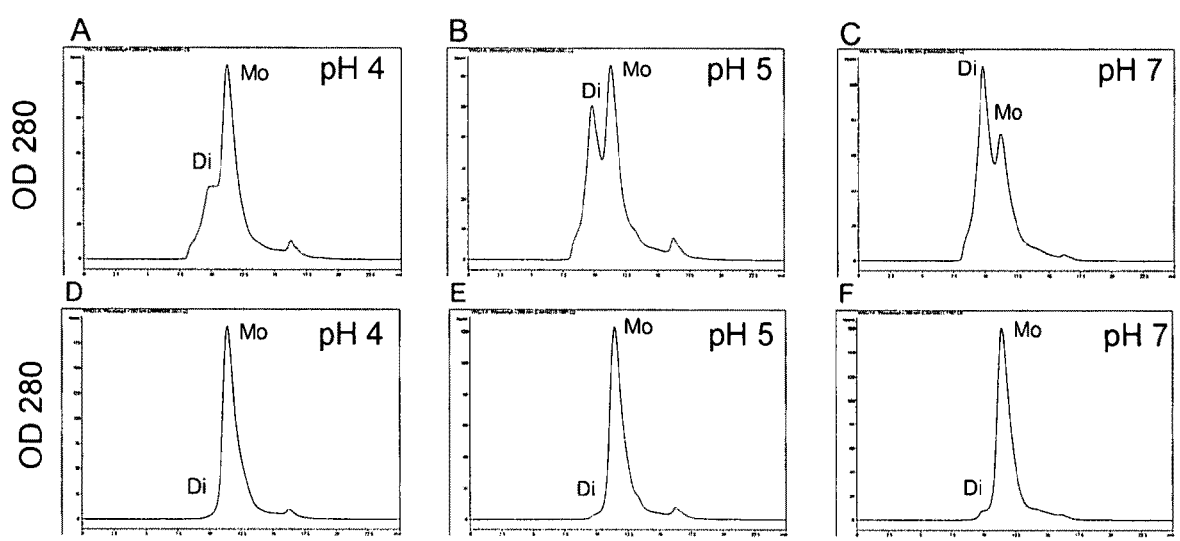
Figure 7:
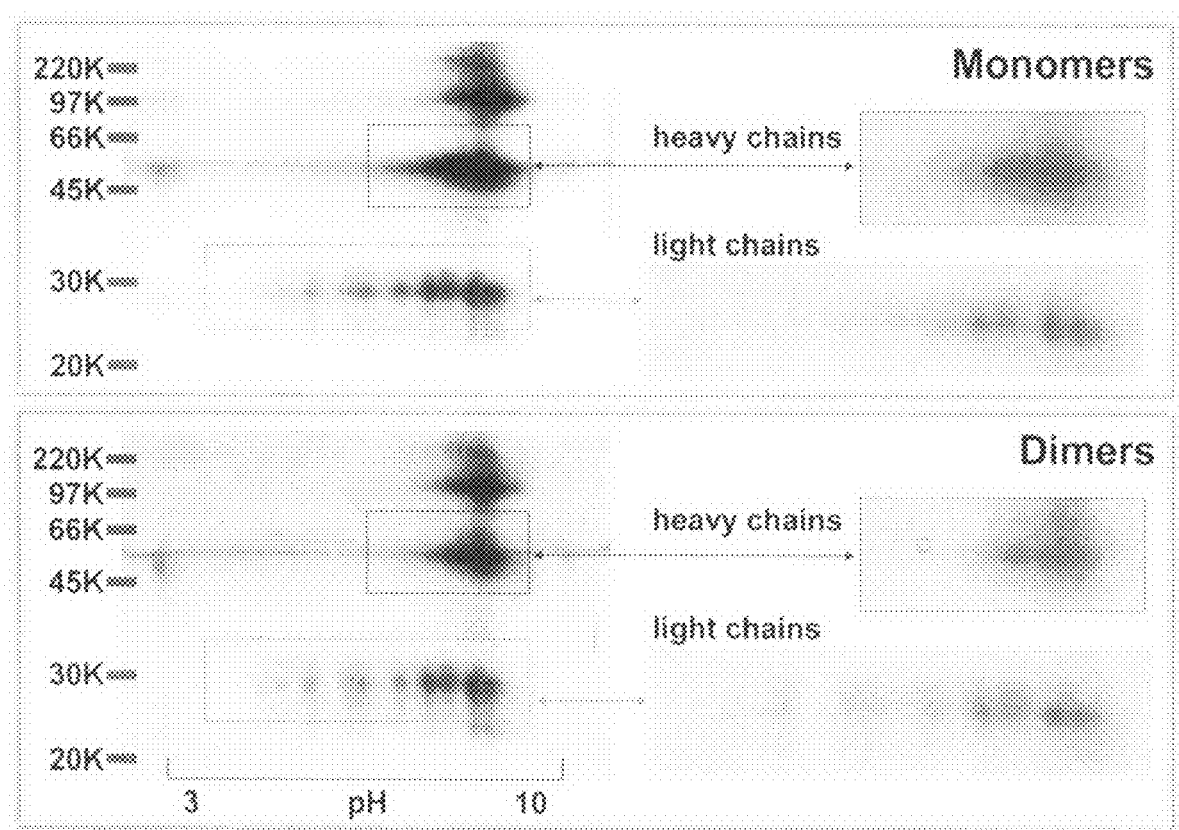
Figure 9:
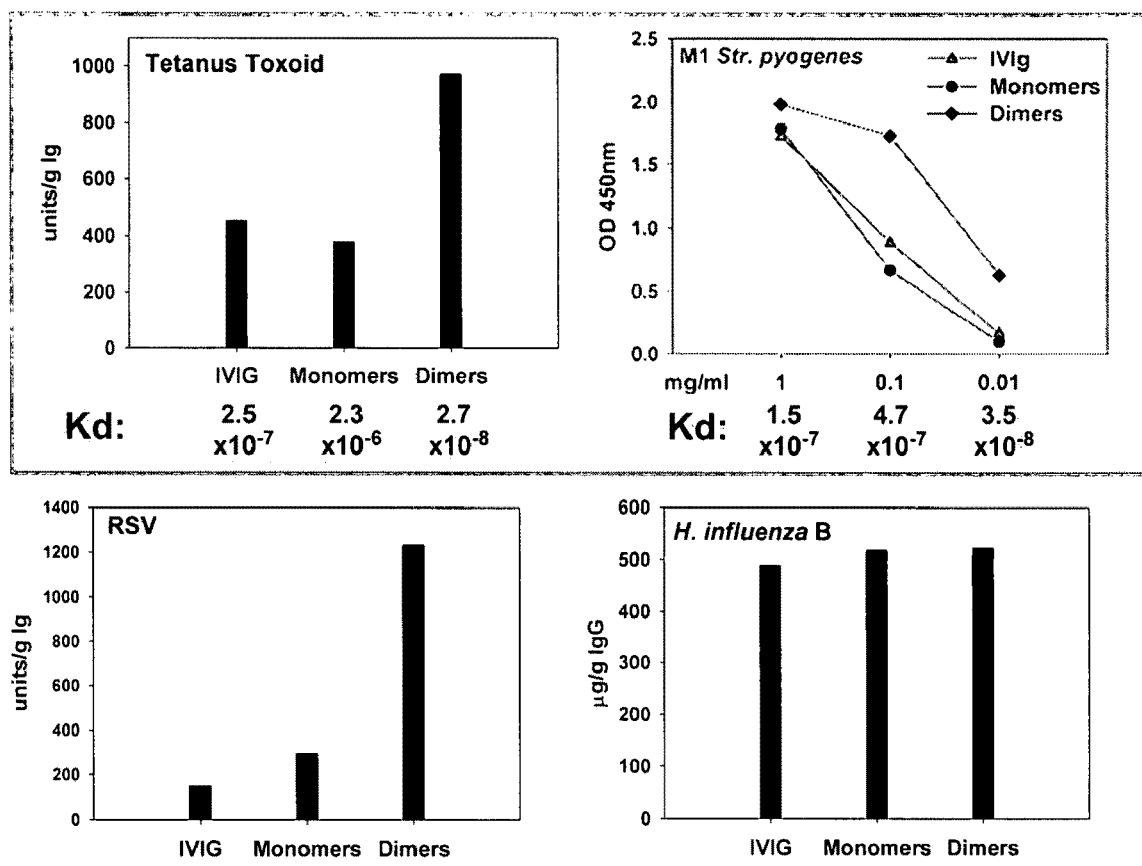
FIG. 9 shows results for the exoantigens Tetanus toxoid, M1 of *S. pyogenes*, RSV and *H. influenzae* B. The dimers show clearly enhanced reactions, confirmed by affinity measurements except for *H. influenzae* B which shows equal reactivity in both fractions.
Figure 10:
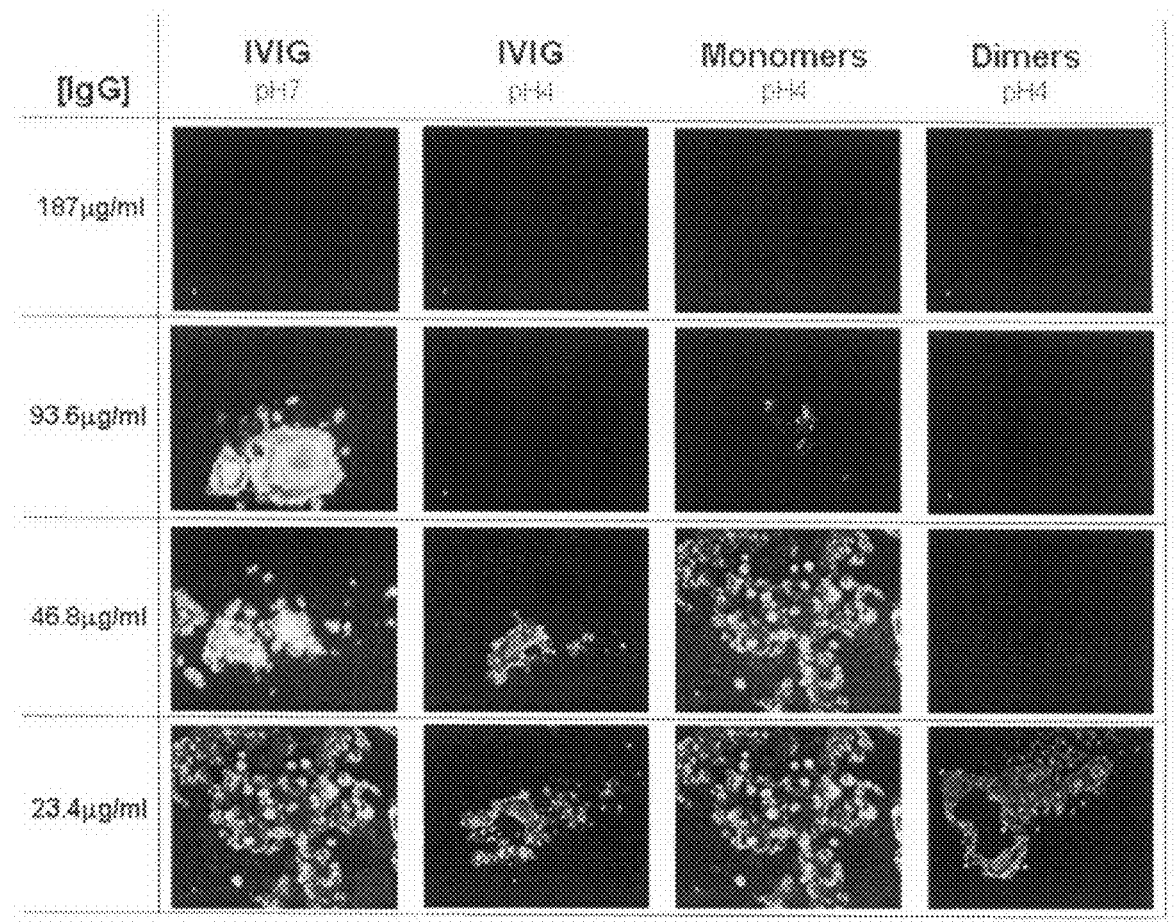

FIG. 10 shows the increased anti-RSV activity in the dimers compared to the monomers. The neutralising action of IVIG non-separated at pH7 and at pH4, monomers at pH4 and dimers at pH4 was assessed. These four IVIG fractions were titrated in order to determine the IgG-concentration at which >90% of the HEp-2 cells were protected from infection. Detection of RSV infection of the HEp-2 cells was clearly indicated by immune fluorescence staining (FIG. 10). A clear dose dependence which varies according to the IVIG fraction being tested was seen. The most striking difference in neutralising activity was seen in a comparison of monomers and dimers at pH4. Significantly more monomers (187 µg/ml) than dimers (46.8 µg/ml) were needed for a 100% neutralisation of the same amount of RSV particles.

Figure 11:
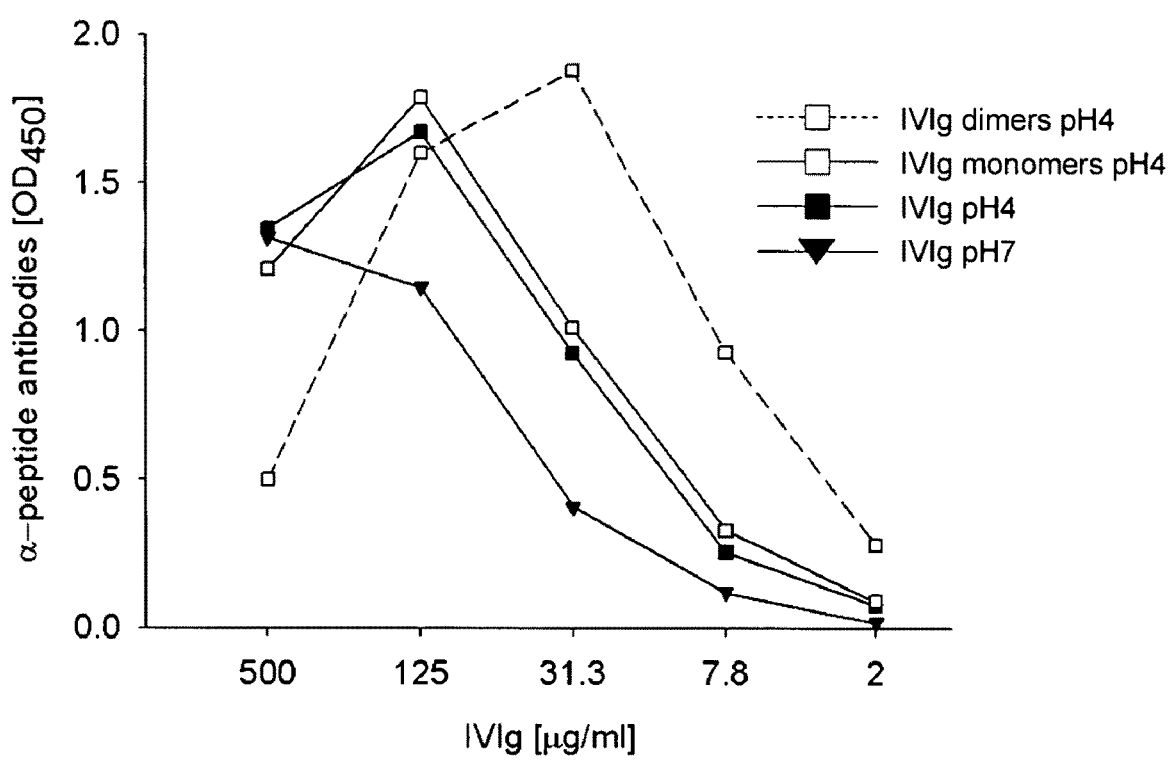

FIG. 11 shows an increased activity in the dimers compared to the monomers against an M3R peptide, one of the target antigens of Sjögrens Syndrome. Autoantibodies against the M3R are present in IVIG preparations, more particularly in the dissociated dimers, suggesting the presence of an anti-idiotypic control of such autoantibodies under normal physiological conditions.

Figure 12:
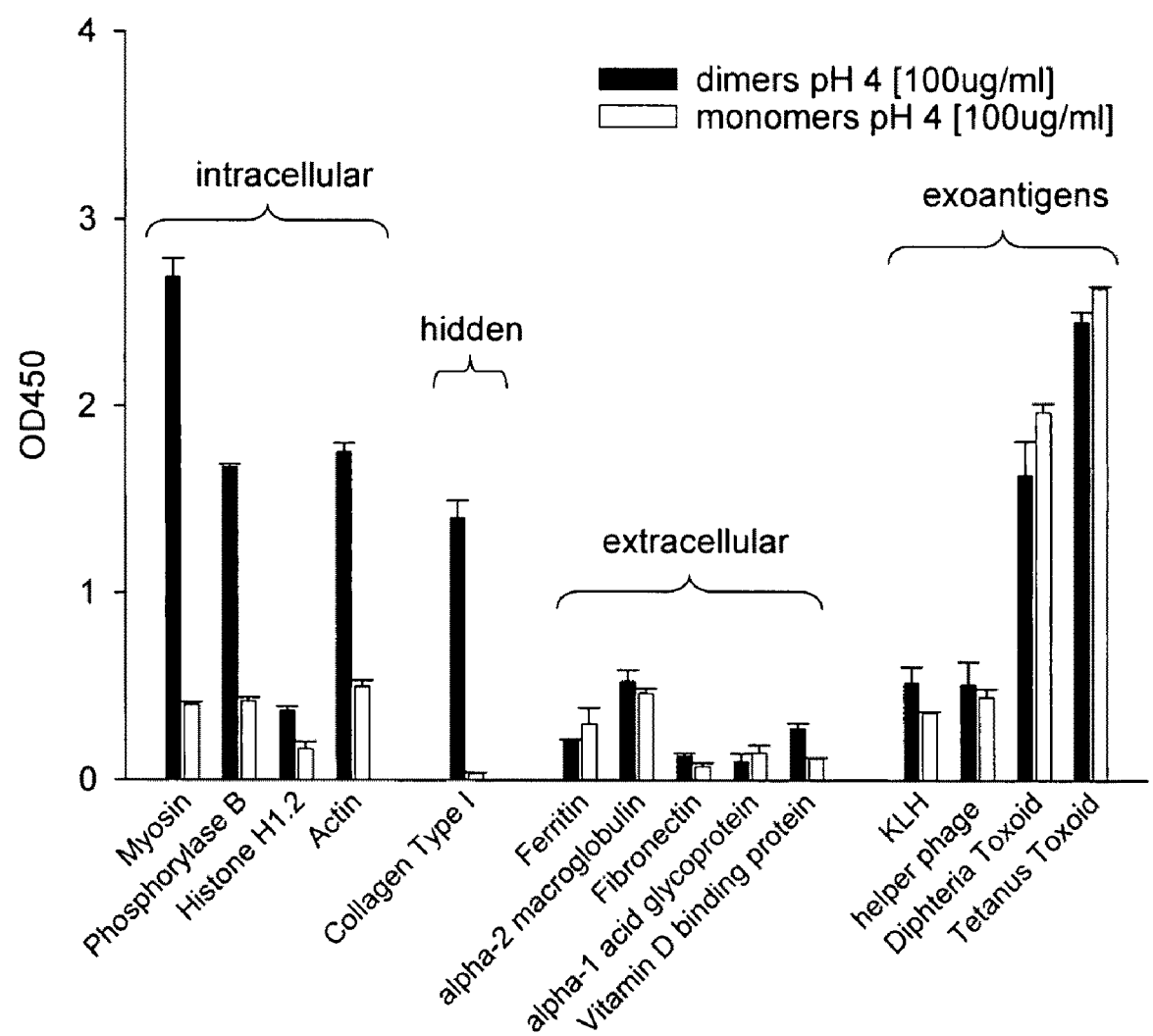

FIG. 12 shows a preferential reactivity of the dimers on self antigens located in the intracellular compartment as compared to extracellular self antigens.

Figure 13:
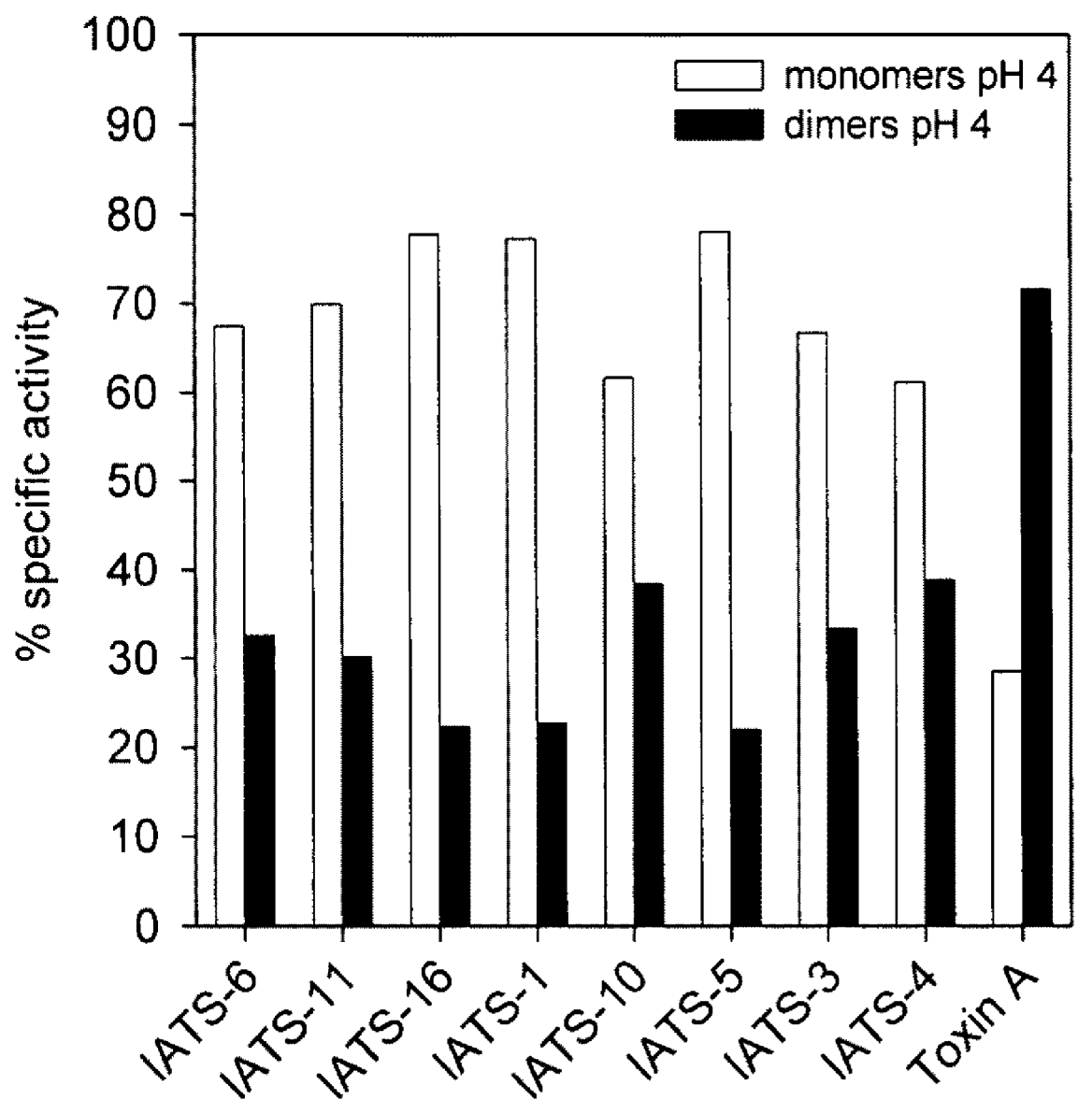

FIG. 13 shows a clear increased activity of the monomers against the various lipopolysaccharide serotypes (represented by IATS classification) of *Pseudomonas aeruginosa*. In comparison the dimers showed an increased activity against the protein, Toxin A.

Figure 14:
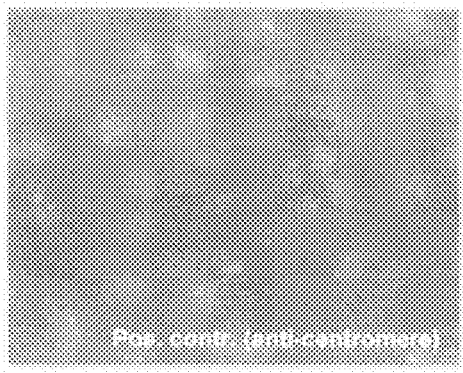
Figure 14:
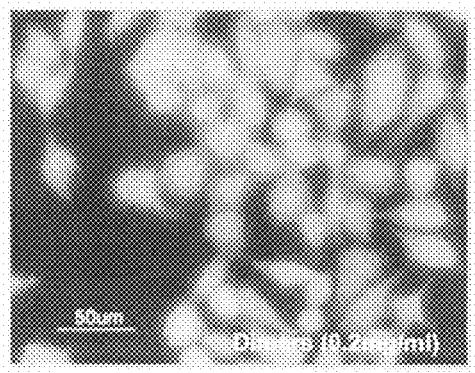
Figure 14:
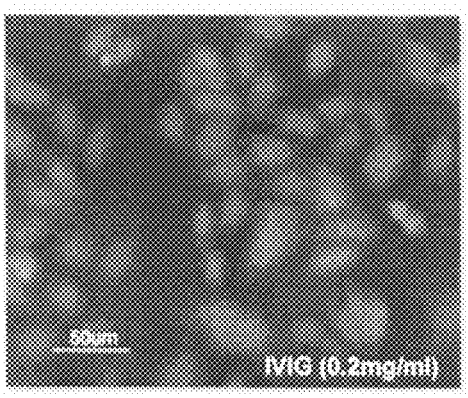
Figure 14:
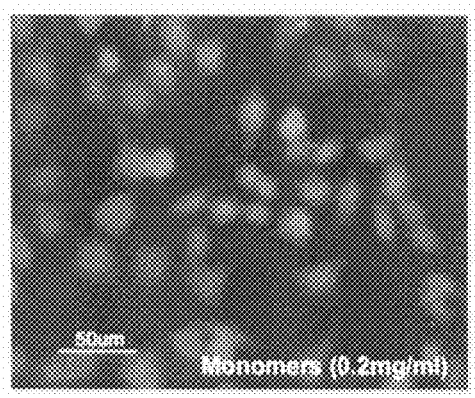

FIG. 14 shows results using the HEp-2 cells for immunohistological analysis. These cells are routinely used by diagnostic laboratories to detect autoantibodies, found in various autoimmune diseases reacting with a range of nuclear, ribosomal and mitochondrial antigens. No pathological pattern of reactivity was seen. Instead there was a marked activity of the dimeric fraction which at higher magnification looked like cytoskeletal components of the cell.

Figure 15:
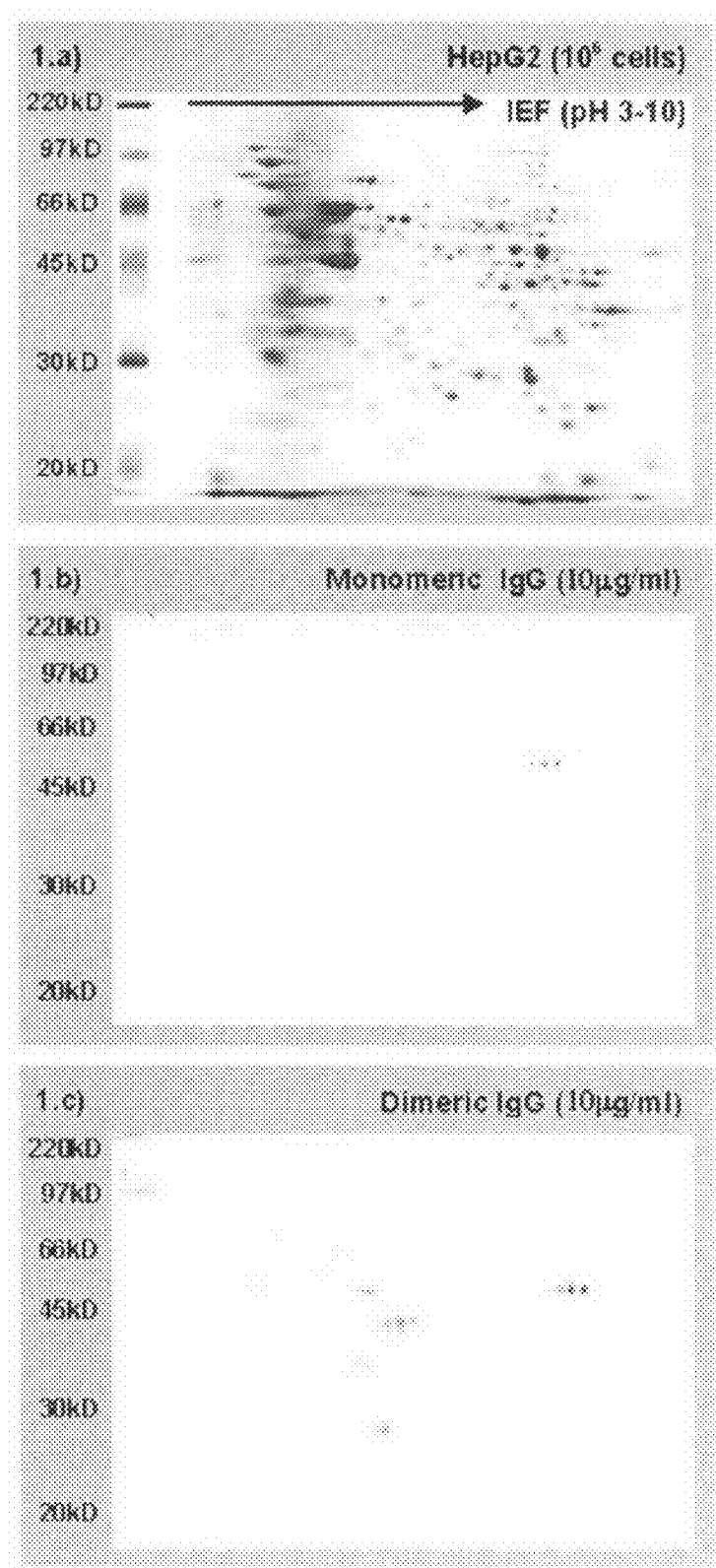

FIG. 15 confirms results previously observed by immunofluorescence on HEp-2 (epithelial) cells. This figure shows a 2D analysis of the proteome of HepG2 cells followed by Western blotting using either the monomeric or dimeric fractions. An increase of autoreactivity in the dimeric as compared to the monomeric fraction is seen. This increase in reactivity is due to a restricted and distinct immunodominant subset of autoantigens as determined by spot picking and analysis by mass spectrometry.

Figure 16:
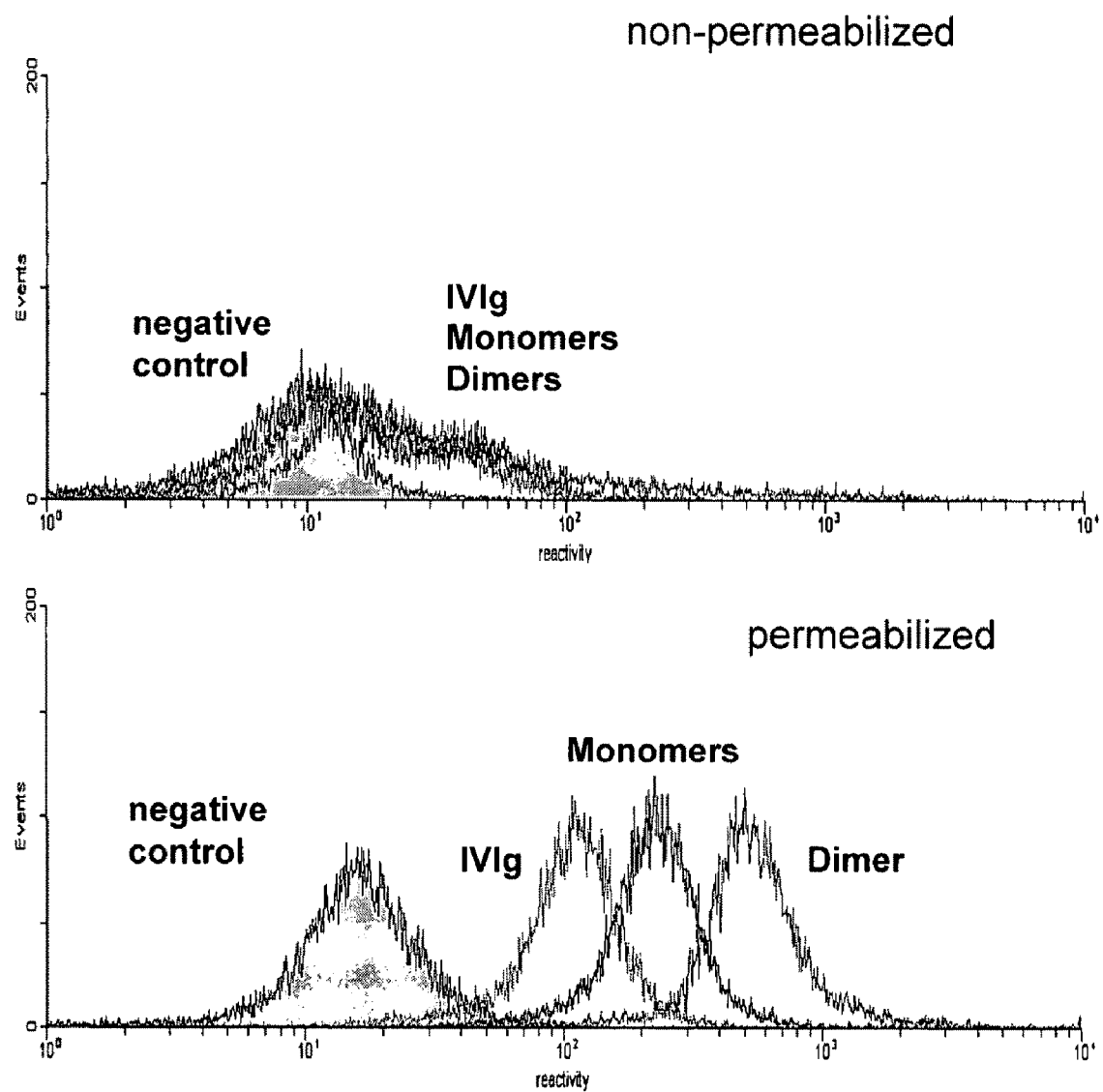

FIG. 16 shows results from FACS analysis on different types of epithelial cells. Cells were either not treated or treated i.e. permeabilized to allow distinction between membrane and intracellular staining respectively. The dimers show increased intracellular reactivity for all the epithelial cells tested. No significant staining over background was seen for the non-permeabilized cells indicating a lack of reactivity with membrane proteins for all fractions tested. In contrast the non-treated RBL cells used as a control non.epithelial cell line (profile not shown) showed equal staining by all the fractions probably representing interaction with Fc-gamma receptors. Table 1 represents cumulative data from both ELISA and Immunodot assays where the respective antigens are immobilized and allowed to react with a concentration range of monomers, dimers and IVIG start preparation as control. To allow a convenient comparison the monomers and dimers have been compared on a simple reactivity scale (++ to −). Differential reactivities are clearly seen between the monomers and dimers. It also seems that some self antigens e.g. myosin and phosphorylase B, while reacting with the monomers also show an increased reactivity with the dimers.

SUMMARY

Based on the above results, the dimeric fraction contains the more mature antibody repertoire and shows remarkable activity against intracellular self-antigens. In contrast the monomeric fraction, which consists of both immune and natural antibodies, may preferentially react with some polysaccharide antigens.

The dimeric fraction contains higher affinity antibodies and thus this fraction would also be biologically more active e.g. neutralising activity in the case of anti-bacterial, -toxin or -viral antibodies. Thus the dimeric fraction represents a subfraction of IVIG with a higher specific activity to certain antigens. This would also account for the presence of anti-idiotype antibodies in this fraction, as the immune system has to respond to the high affinity antibodies being produced by a negative feedback or down regulation to maintain homeostasis.

The monomeric fraction contains the lower affinity antibodies providing the natural antibodies i.e. the basic repertoire from which the high affinity antibodies must develop.

REFERENCES

1. Coutinho, A., M. D. Kazatchkine, and S. Avrameas, *Natural autoantibodies*. Curr Opin Immunol, 1995. 7(6): p. 812-8.
2. Kazatchkine, M. D. and S. V. Kaveri, *Immunomodulation of autoimmune and inflammatory diseases with intravenous immune globulin*. N Engl J Med, 2001. 345(10): p. 747-55.
3. Cohen, I. R., *The cognitive paradigm and the immunological homunculus*. Immunol Today, 1992.13(12): p. 490-4.
4. Haeney M. *Intravenous immune globulin in primary immunodeficiency*. Clin Exp Immunol, 1994, 97: p. 11-15.
5. Sewell, W. A. and S. Jolles, *Immunomodulatory action of intravenous immunoglobulin*. Immunology, 2002.107(4): p. 387-93.
6. Rossi, F., G. Dietrich, and M. D. Kazatchkine, *Anti-idiotypes against autoantibodies in normal immunoglobulins: evidence for network regulation of human autoimmune responses*. Immunol Rev, 1989.110: p. 135-49.
7. Vassilev, T. L., et al., *Variable region-connected, dimeric fraction of intravenous immunoglobulin enriched in natural autoantibodies*. J Autoimmun, 1995. 8(3): p. 405-13.
8. Simon, H. U. and P. J. Spath, *IVIG-mechanisms of action*. Allergy, 2003. 58(7): p. 543-52.
9. Ginaldi, L., et al., *The immune system in the elderly: activation-induced and damage-induced apoptosis*. Immunol Res, 2004. 30(1): p. 81-94.
10. Lacroix-Desmazes, S., et al., *Analysis of the natural human IgG antibody repertoire: life-long stability of reactivities towards self antigens contrasts with age-dependent diversification of reactivities against bacterial antigens*. Eur J Immunol, 1995.25(9): p. 2598-604.
11. Tankersley, D. L., *Dimer formation in immunoglobulin preparations and speculations on the mechanism of action of intravenous immune globulin in autoimmune diseases*. Immunol Rev, 1994.139: p. 159-72.

The references cited above are all incorporated by reference.

The invention claimed is:

1. An isolated fraction of human antibodies from a heterogeneous human donor population, obtained by a method comprising the following steps:
   (a) subjecting a human antibody preparation from a heterogeneous donor population to a size fractionation,
   (b) recovering a fraction of dimeric antibodies, wherein purity of the dimeric antibody fraction is at least 75% and wherein purity analysis is carried out immediately after size fractionation,
   (c) monomerizing the dimeric antibodies having an apparent molecular weight of about 300 kDa to produce remonomerized antibodies, and
   (d) optionally admixing the remonomerized antibodies with a pharmaceutically acceptable carrier or excipient.

2. The fraction of claim 1, wherein the human antibody preparation is a polyclonal human immunoglobulin preparation.

3. The fraction of claim 1, wherein the fraction of human antibodies is a fraction of dimeric antibodies from an intravenous polyclonal human immunoglobulin preparation (IVIG).

4. The fraction of claim 1, wherein the fraction of human antibodies has at least a two fold higher reactivity to exoantigens and/or autoantigens than the heterogeneous human donor population.

5. The fraction of claim 1, wherein step (a) comprises size exclusion separation, gel filtration, ultrafiltration, and/or other gel or membrane separation methods.

6. The fraction of claim 1, wherein purity of the dimeric antibody fraction recovered in step (b) is at least 80% and wherein the purity analysis is carried out immediately after size fractionation.

7. The fraction of claim 1, wherein purity of the dimeric antibody fraction recovered in step (b) is at least 85% and wherein the purity analysis is carried out immediately after size fractionation.

8. The fraction of claim 1, wherein step (c) comprises adjusting to an acidic pH.

9. The fraction for claim 8, wherein the acidic pH is in a range of about 3 to about 5.

10. The fraction of claim 1, wherein the fraction has 10% or less dimers after monomerization.

11. The fraction of claim 1, wherein the remonomerized antibodies do not comprise F(ab')$_2$ fragments obtained by proteolytic digestion.

12. The fraction of claim 1, wherein the fraction of human antibodies has 5% or less dimers after monomerization.

13. A method for manufacturing a pharmaceutical composition comprising a fraction of human antibodies from a heterogeneous human donor population comprising:
 (a) subjecting a human antibody preparation from a heterogeneous donor population to a size fractionation;
 (b) recovering a fraction of dimeric antibodies, wherein purity of the dimeric antibody fraction is at least 75% and wherein purity analysis is carried out immediately after size fractionation,
 (c) monomerizing the dimeric antibodies having an apparent molecular weight of about 300 kDa to produce remonomerized antibodies, and
 (d) optionally admixing the remonomerized antibodies with a pharmaceutically acceptable carrier or excipient.

14. The method of claim 13 wherein step (a) comprises size exclusion separation, gel filtration, ultrafiltration, and/or other gel or membrane separation methods.

15. The method of claim 13, wherein step (c) comprises adjusting to an acidic pH.

16. The method of claim 15, wherein the acidic pH is in a range of about 3 to about 5.

* * * * *